United States Patent [19]

Noyori

[11] 4,284,581
[45] Aug. 18, 1981

[54] LITHIUMALUMINIUM HYDRIDE COMPOUNDS

[75] Inventor: Ryoji Noyori, Aichi, Japan

[73] Assignee: Ono Pharmaceutical Co., Ltd., Osaka, Japan

[21] Appl. No.: 82,240

[22] Filed: Oct. 5, 1979

[30] Foreign Application Priority Data

Oct. 12, 1978 [JP] Japan ................................ 53-124704
May 10, 1979 [JP] Japan ................................ 54-56299

[51] Int. Cl.³ ............................................... C07F 5/06
[52] U.S. Cl. ............................................ 260/448 AD
[58] Field of Search ............. 260/448 AD; 252/431 L

[56] References Cited

U.S. PATENT DOCUMENTS

| | | | |
|---|---|---|---|
| 2,844,551 | 7/1958 | Orthner et al. | 260/448 AD X |
| 3,060,216 | 10/1962 | Hamprecht et al. | 260/448 AD |
| 3,147,272 | 9/1964 | Brown | 260/448 AD |
| 3,652,622 | 3/1972 | Vit et al. | 260/448 AD |
| 3,686,249 | 8/1972 | Hartmann | 260/448 AD |
| 3,787,450 | 1/1974 | Casensky et al. | 260/448 AD X |

OTHER PUBLICATIONS

Chemical Abstracts, vol. 93, 149842d (1980), (re: Tennen Yuki Kagobutsu Toronkai Koen Yoshishu, 22nd, publ. Sep. 20, 1979).
Tetrahedron 32, 939–944, (1976).
JACS 101, 3129–3131, (1979).

*Primary Examiner*—H. M. S. Sneed
*Attorney, Agent, or Firm*—Stevens, Davis, Miller & Mosher

[57] ABSTRACT

Lithium 1,1'-binaphthyl-2,2'-dioxyaluminium hydride compounds of the general formula:

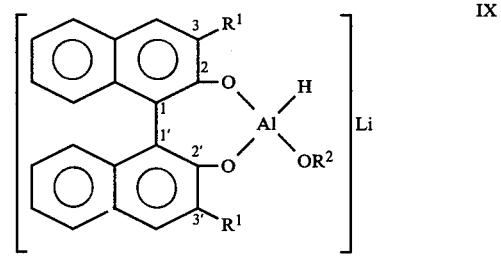

IX wherein $R^1$ represents a hydrogen atom, or a methyl or ethyl group, and $R^2$ represents a straight- or branched-chain alkyl group containing from 1 to 12 carbon atoms unsubstituted or substituted by at least one fluorine atom, hydroxy group, or straight- or branched-chain alkoxy group containing from 1 to 4 carbon atoms, or represents a phenyl group unsubstituted or substituted by at least one straight- or branched-chain alkyl group containing from 1 to 4 carbon atoms are useful as reducing agents.

24 Claims, No Drawings

LITHIUMALUMINIUM HYDRIDE COMPOUNDS

This invention relates to new lithium 1,1'-binaphthyl-2,2'-dioxyaluminium hydride compounds, to a process for their preparation and their use as reducing agents.

Reducing agents for the conversion of an oxo group into a hydroxy group are well known, for example sodium borohydride, potassium borohydride, lithium borohydride, zinc borohydride, lithium tri-tert-butoxyaluminium hydride, lithium trimethoxyaluminium hydride and sodium cyanoborohydride. When these known reducing agents are used to reduce a ketone, a centre of chirality may be produced, but the alcohol product is generally in the racemic form, consisting of an equimolecular mixture of the R- and S-isomers. It is sometimes the case that one of the isomers is useful and the other isomer is not. In particular in the industrial preparation of the prostaglandins or prostaglandin analogues useful in human or veterinary medicine, one of the isomers is used and the other is not.

Prostaglandins are derivatives of prostanoic acid and may be named by reference to its formula:

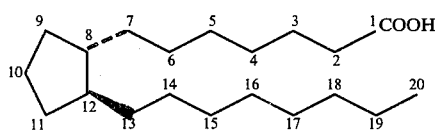

In the reduction of prostaglandin E analogues, substituted by an oxo group at the $C_9$ position, e.g. prostaglandin $E_2$ of the formula:

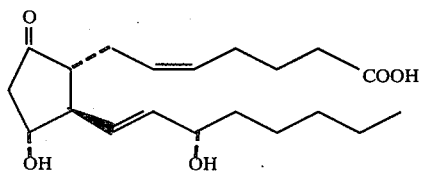

the corresponding prostaglandin $F_\alpha$ analogues, e.g. prostaglandin $F_{2\alpha}$ of the formula:

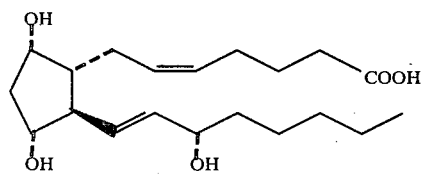

are of importance, and the other isomers, i.e. prostaglandin $F_\beta$ analogues, e.g. prostaglandin $F_{2\beta}$ of the formula:

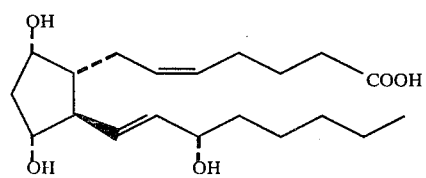

are of limited significance. Methods for the stereoselective reduction of the $C_9$-oxo group have been studied, for example the method described in J. Amer. Chem. Soc., 93, 7319 (1971).

In the reduction of prostaglandins or prostaglandin analogues, substituted by an oxo group at the $C_{15}$ position or the reduction of compounds or intermediates used in their synthesis, for example an intermediate of the formula:

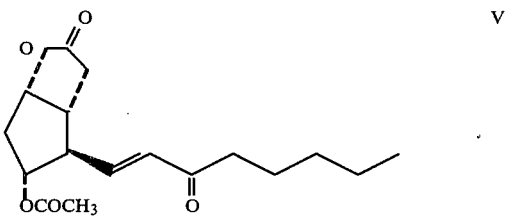

or a 3-oxo compound of the formula:

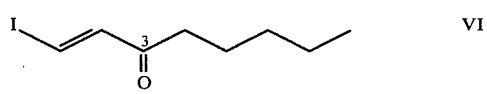

the corresponding 15α-hydroxy intermediates, e.g. the intermediate of the formula:

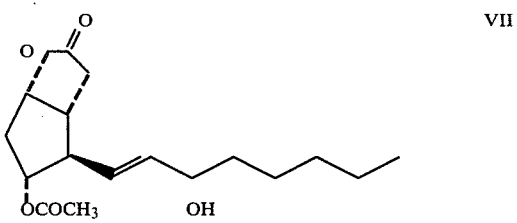

or the 3α-hydroxy compound of the formula:

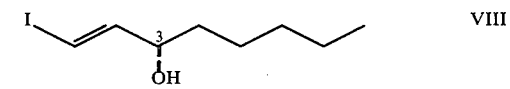

are used, and the other isomers, i.e. the 15β-hydroxy intermediates and 3β-hydroxy compounds, are not used.

The 15β-hydroxy or 3β-hydroxy compounds are inverted into the corresponding 15α-hydroxy or 3α-hydroxy compounds, or converted to the 15-oxo or 3-oxo compounds and then reduced again to produce a proportion of 15α- or 3α-compound, or they may be discarded. Methods of stereoselective reduction of the $C_{15}$-oxo group have been investigated, for example the method described in J. Amer. Chem. Soc., 94, 8616 (1972). A useful method for the stereoselective reduction of the compound of formula VI is not yet known [cf. "Prostaglandin Synthesis", pp. 116–119 (1977), Academic Press, Inc., New York].

The stereoselective reducing agents which are already known have several disadvantages from the industrial and commercial viewpoints. For example, widespread investigations have been carried out in order to discover new reducing agents possessing high stereoselectivity more than 60%. As a result of extensive research and experimentation, it has been found that certain lithium 1,1'-binaphthyl-2,2'-dioxyaluminium hydride compounds have high stereoselectivity.

The present invention accordingly provides lithium 1,1'-binaphthyl-2,2'-dioxyaluminium hydride compounds of the general formula:

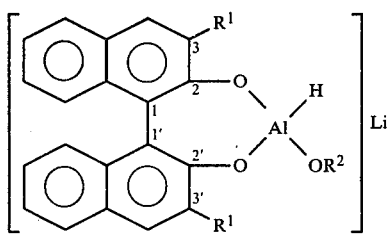
IX (wherein $R^1$ represents a hydrogen atom, or a methyl or ethyl group, and $R^2$ represents a straight- or branched-chain alkyl group containing from 1 to 12 carbon atoms unsubstituted or substituted by at least one fluorine atom, hydroxy group, or straight- or branched-chain alkoxy group containing from 1 to 4 carbon atoms, or represents a phenyl group unsubstituted or substituted by at least one straight- or branched-chain alkyl group containing from 1 to 4 carbon atoms) which are useful as reducing agents for the conversion, particularly the stereoselective conversion, of an organic compound having a carbonyl group, e.g. a ketone or aldehyde, into the corresponding alcohol.

The present invention is concerned with all compounds of general formula IX in the R- or S-configuration, or mixtures thereof, more particularly the racemic form, consisting of equimolecular mixtures of the R- and S-isomers. Compounds of general formula IX in the R- or S-configuration are preferred.

The straight- or branched-chain alkyl group containing from 1 to 12 carbon atoms represented by $R^2$ may be methyl, ethyl, propyl, butyl, pentyl, hexyl, heptyl, octyl, nonyl, decyl, undecyl, dodecyl or their isomers.

The straight- or branched-chain alkyl group containing from 1 to 4 carbon atoms, and the straight- or branched-chain alkyl moiety of the straight- or branched-chain alkoxy group containing from 1 to 4 carbon atoms in the definition of $R^2$ may be methyl, ethyl, propyl, isopropyl, butyl, isobutyl, sec-butyl or tert-butyl.

Preferred compounds of general formula IX are those wherein $R^1$ represents a hydrogen atom or a methyl group and $R^2$ preferably represents a straight- or branched-chain alkyl group containing from 1 to 12 carbon atoms or an alkyl group containing from 2 to 4 carbons substituted by at least one fluorine atom or by a hydroxy or straight- or branched-chain alkoxy group containing from 1 to 4 carbon atoms, or represents a phenyl group substituted by two straight- or branched-chain alkyl groups containing from 1 to 4 carbon atoms; more preferably $R^2$ represents a straight- or branched-chain alkyl group containing from 1 to 4 carbon atoms, especially methyl or ethyl.

According to a feature of the present invention, the lithium 1,1'-binaphthyl-2,2'-dioxyaluminium hydride compounds of general formula IX, wherein the various symbols are as hereinbefore defined, are prepared by reaction of a 2,2'-dihydroxy-1,1'-binaphthyl compound of the general formula:

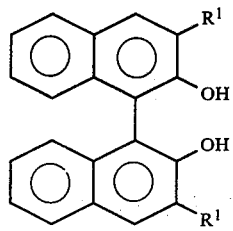
X (wherein $R^1$ is as hereinbefore defined) with one equimolar amount of lithiumaluminium hydride and of an alcohol of the general formula:

$R^2$—OH    XI wherein $R^2$ is as hereinbefore defined.

The reaction is generally carried out under an atmosphere of an inert gas, e.g. nitrogen or argon, and under anhydrous conditions, in an inert organic solvent, particularly an aprotic solvent, e.g. diethyl ether, tetrahydrofuran or diglyme, preferably tetrahydrofuran, at a temperature from 0° to 100° C., preferably at room temperature.

The reaction is completed with the evolution of three equivalents of hydrogen gas, and the mixture obtained should be used in a reduction process as a solution of the reducing agent of general formula IX without isolation. This solution containing the reducing agent may be prepared immediately before use, or may be previously prepared and stored under an atmosphere of an inert gas at a temperature below room temperature.

The 2,2'-dihydroxy-1,1'-binaphthyl compound of general formula X, wherein $R^1$ represents a hydrogen atom, has two isomers, i.e. the R- and S-isomers, and each isomer may be separated from the racemic compound, consisting of an equimolecular mixture of the R- and S-isomers, by the method described in Tetrahedron Letters, 4617 (1971). The racemic compound of general formula X, wherein $R^1$ represents a hydrogen atom, may be prepared by the method described in Chemische Berichte, 59,2159 (1926).

The R- or S-isomer or a mixture of those isomers of the 2,2'-dihydroxy-1,1'-binaphthyl compounds of general formula X, wherein $R^1$ represents a methyl or ethyl group, may be prepared from the corresponding isomers or a mixture of the isomers of the 2,2'-dihydroxy-1,1'-binaphthyl compound of general formula X, wherein $R^1$ represents a hydrogen atom, by the series of reactions depicted schematically below in Scheme A, wherein $R^3$ represents a methyl or ethyl group.

SCHEME A

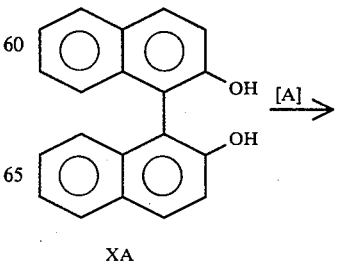

XA

-continued

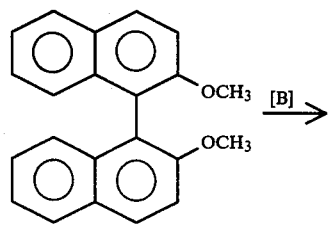

XI

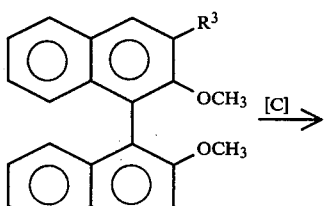

XII

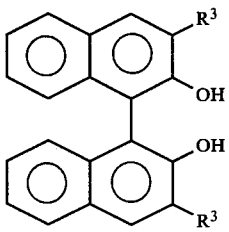

XB

Referring to Scheme A, the conversion [A] may be carried out by methods known per se for the conversion of a hydroxy group into a methoxy group, for example by reaction with potassium hydride and methyl iodide in tetrahydrofuran at room temperature. By the expression "methods known per se" as used in this specification is meant methods heretofore used or described in the chemical literature.

The conversion [B] may be carried out with butyllithium-N,N,N',N'-tetramethylethylenediamine complex in an inert organic solvent, e.g. tetrahydrofuran, at a temperature from 0° to 50° C., followed by reaction with a methyl or ethyl halide, e.g. methyl iodide or ethyl bromide, at room temperature.

The conversion [C] may be carried out by methods known per se for the conversion of a methoxy group into a hydroxy group, for example by reaction with boron tribromide in an inert organic solvent, e.g. methylene chloride, at a temperature ranging from ambient to −78° C.

According to a further feature of the present invention, the compounds of this invention may be used as a reducing agent for the conversion of an organic compound having a carbonyl group, i.e. a ketone or aldehyde, into the corresponding alcohol.

In general, the compounds of the present invention react only with the carbonyl group of organic compounds, which may also have in their molecule halogen atoms or additional functional groups, for example ester, carboxyl, amido, amino, hydroxy, ether, enyl (i.e. double bonds) or ynyl (i.e. triple bonds) groups, without any side-reactions involving such additional functional groups. For that reason, the compounds of the invention may be used in the reduction of very many compounds having a carbonyl group.

The compounds may also be used for the selective reduction of one of the carbonyl groups in certain compounds which possess, e.g. two carbonyl groups in the molecule. For example, when (E)-2-oxa-6-syn-(3-oxo-oct-1-enyl)-7-anti-(tetrahydropyran-2-yloxy)-cis-bicyclo[3.3.0]octan-3-one is reduced using a compound according to the invention the 3-oxo-octenyl grouping is reduced to a 3-hydroxyoctenyl grouping whereas the 3-oxo group in the bicyclo-octan-3-one grouping is unaffected (and requires a stronger reducing agent such as diisobutylaluminium hydride for its reduction).

Preferred organic compounds for reduction by the compounds of the invention are prochiral ketones or enones, i.e. ketones which convert into chiral alcohols by reduction, because the reduction of the prochiral ketone, especially, in the case of prostaglandins, prostaglandin analogues or their intermediates, with the S- or R-isomer of this invention produces stereoselectively the S- or R-alcohol.

Particularly preferred organic compounds are prostaglandins, prostaglandin analogues, thromboxanes and thromboxane analogues, that is to say, compounds having the prostane skeleton of the formula:

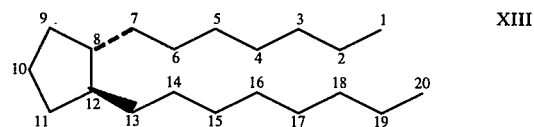

XIII or, a homo- or nor-prostane skeleton (i.e. the prostane skeleton in which one or more methylene groups are added to, or eliminated from the alkyl side chains and/or the cyclopentane ring of the prostane skeleton) or a thia-, aza- or oxa-prostane (or homo- or nor-prostane) skeleton (i.e. the skeleton in which one or more carbon atoms of the prostane, homo- or nor-prostane skeleton is replaced by one or more sulphur, nitrogen or oxygen atoms) and intermediates for their preparation and compounds of the general formula:

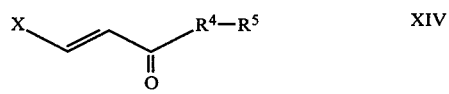

XIV wherein X represents a halogen atom, preferably a bromine or iodine atom, the double bond is trans, $R^4$ represents a single bond, or a straight- or branched-chain alkylene group containing from 1 to 5 carbon atoms, and $R^5$ represents a hydrogen atom, or a straight- or branched-chain alkyl or alkoxy group containing from 1 to 8 carbon atoms, or a cycloalkyl or cycloalkoxy group containing from 4 to 7 carbon atoms unsubstituted or substituted by at least one straight- or branched-chain alkyl group containing from 1 to 8 carbon atoms, or a phenyl or phenoxy group unsubstituted or substituted by at least one halogen atom, trifluoromethyl group or straight- or branched-chain alkyl group containing from 1 to 4 carbon atoms, with the proviso that, when $R^4$ represents a single bond, $R^5$ is not alkoxy, cycloalkoxy or phenoxy.

Preferred prostaglandin compounds for reduction by the compounds of the invention are those in which, in the prostane skeleton (or the prostane skeleton modified as detailed above), the n-pentyl group attached to the 15-position is replaced by a group —R⁴—R⁵ wherein R⁴ and R⁵ are as hereinbefore defined.

The oxo group or groups to be reduced are preferably at the 9, 11 or, most preferably, 15-position of the prostane skeleton (or of the prostane skeleton modified as outlined above).

In the reduction of compounds of general formula XIV wherein R⁴ and R⁵ are as hereinbefore defined the reductant is preferably in the R- or, most preferably, the S-configuration.

Preferred intermediates for reduction by the compounds of the invention are those of the formulae:

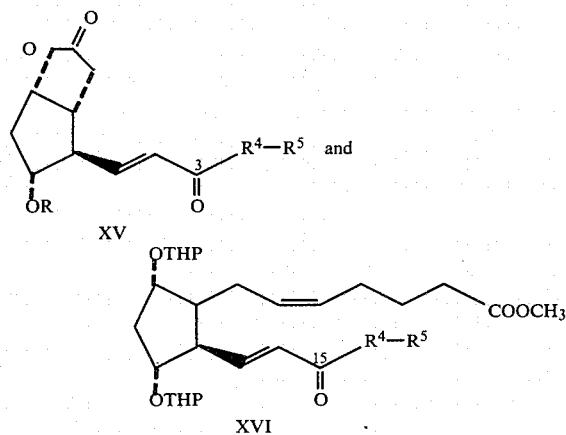

wherein R represents a hydrogen atom, or an acetyl or tetrahydropyranyl group, THP represents a tetrahydropyranyl group, and R⁴ and R⁵ are as hereinbefore defined. The 3-oxo and 15-oxo groups in formulae XV and XVI may be reduced stereoselectively to 3α-hydroxy and 15α-hydroxy groups respectively.

Preferably the grouping —R⁴—R⁵ represents, for example methyl, ethyl, 1-methylethyl, propyl, 1-methylpropyl, 2-methylpropyl, 1-ethylpropyl, butyl, 1-methylbutyl, 2-methylbutyl, 3-methylbutyl, 1-ethylbutyl, 2-ethylbutyl, pentyl, 1-methylpentyl, 2-methylpentyl, 3-methylpentyl, 4-methylpentyl, 1,1-dimethylpentyl, 1,2-dimethylpentyl, 1,4-dimethylpentyl, 1-ethylpentyl, 2-ethylpentyl, 1-propylpentyl, 2-propylpentyl, hexyl, 1-methylhexyl, 2-methylhexyl, 1,1-dimethylhexyl, 1-ethylhexyl, 2-ethylhexyl, heptyl, 2-ethylheptyl, nonyl, undecyl, cyclobutyl, 1-propylcyclobutyl, 1-butylcyclobutyl, 1-pentylcyclobutyl, 1-hexylcyclobutyl, 2-methylcyclobutyl, 2-propylcyclobutyl, 3-ethylcyclobutyl, 3-propylcyclobutyl, 2,3,4-triethylcyclobutyl, cyclopentyl, cyclopentylmethyl, 1-cyclopentylethyl, 2-cyclopentylethyl, 2-cyclopentylpropyl, 3-cyclopentylpropyl, 2-pentylcyclopentyl, 2,2-dimethylcyclopentyl, 3-ethylcyclopentyl, 3-propylcyclopentyl, 3-butylcyclopentyl, 3-tert-butylcyclopentyl, (1-methyl-3-propyl)cyclopentyl, (2-methyl-3-propyl)cyclopentyl, (2-methyl-4-propyl)cyclopentyl, cyclohexyl, cyclohexylmethyl, 1-cyclohexylethyl, 2-cyclohexylethyl, 3-cyclohexylpropyl, (1-methyl-2-cyclohexyl)ethyl, 2-cyclohexylpropyl, (1-methyl-1-cyclohexyl)ethyl, 4-cyclohexylbutyl, 3-ethylcyclohexyl, 3-isopropylcyclohexyl, 4-methylcyclohexyl, 4-ethylcyclohexyl, 4-propylcyclohexyl, 4-tert-butylcyclohexyl, 2,6-dimethylcyclohexyl, 2,2-dimethylcyclohexyl, (2,6-dimethyl-4-propyl)cyclohexyl, 1-methylcyclohexylmethyl, cycloheptyl, cycloheptylmethyl, 1-cycloheptylethyl, 2-cycloheptylethyl, phenyl, benzyl, 1-phenylethyl, 2-phenylethyl, 3-phenylpropyl, 4-phenylbutyl, 5-phenylpentyl, (1-methyl-2-phenyl)ethyl, (1,1-dimethyl-2-phenyl)ethyl, (1-methyl-1-phenyl)ethyl, 1-phenylpentyl, phenoxymethyl, 2-phenoxyethyl, 3-phenoxypropyl, 4-phenoxybutyl, 5-phenoxypentyl, 3-chlorophenoxymethyl, 4-chlorophenoxymethyl, 4-fluorophenoxymethyl, 3-trifluoromethylphenoxymethyl, 2-methylphenoxymethyl, 3-methylphenoxymethyl, 4-methylphenoxymethyl, 4-ethylphenoxymethyl, 4-tert-butylphenoxymethyl, 4-sec-butylphenoxymethyl, propoxymethyl, isopropoxymethyl, butoxymethyl, pentyloxymethyl, hexyloxymethyl, 1-ethoxyethyl, 1-propoxyethyl, 1-isopropoxyethyl, 1-neopentyloxyethyl, 1-pentyloxyethyl, (1-methyl-1-ethoxy)ethyl, (1-methyl-1-butoxy)ethyl, (1-methyl-1-isobutoxy)ethyl, (1-methyl-1-neopentyloxy)ethyl, (1-methyl-1-butoxy)ethyl, (1-methyl-1-isopentyloxy)ethyl, (1-methyl-1-pentyloxy)ethyl, 2-ethoxyethyl, 2-propoxyethyl, 2-butoxyethyl, 2-(1-ethylbutoxy)ethyl, 2-pentyloxyethyl, 1-ethoxypropyl, 1-propoxypropyl, 1-(2-methylbutoxy)propyl, 1-pentyloxypropyl, 2-methoxypropyl, 3-methoxypropyl, 3-ethoxypropyl, 3-propoxypropyl, 3-sec-butoxypropyl, 3-isobutoxypropyl, 3-butoxypropyl, (1-methyl-2-methoxy)ethyl, (1-methyl-2-ethoxy)ethyl, (1-methyl-2-isobutoxy)ethyl, 1-pentyloxybutyl, (1-pentyloxy-2-methyl)propyl, 4-methoxybutyl, 4-ethoxybutyl, 4-propoxybutyl, (1-methyl-3-methoxy)propyl, (1-methyl-3-propoxy)propyl, (2-methyl-3-methoxy)propyl, (1,1-dimethyl-2-ethoxy)ethyl, (1,1-dimethyl-2-propoxy)ethyl, (1,1-dimethyl-2-isobutoxy)ethyl, 5-methoxypentyl, 5-ethoxypentyl, 1-pentyloxypentyl, (1-ethyl-3-propoxy)propyl, cyclobutyloxymethyl, cyclopentyloxymethyl, cyclohexyloxymethyl, cycloheptyloxymethyl, 2-cyclopentyloxyethyl or 2-cyclohexyloxyethyl.

The reduction according to the present invention is carried out by the reaction of an organic compound possessing a carbonyl group, i.e. a ketone or aldehyde, with the compounds of the invention of general formula IX under an atmosphere of an inert gas, e.g. nitrogen or argon, and under anhydrous conditions in the presence or absence of a tertiary amine, preferably N,N,N',N'-tetramethylethylenediamine, in an inert organic solvent, preferably an aprotic solvent, e.g. diethyl ether, tetrahydrofuran or diglyme, most preferably tetrahydrofuran, at a temperature from −100° to 100° C. The reduction is generally carried out using one or more equivalents, preferably one to five equivalents, of the reducing agents of the general formula IX.

The reduction product may, if desired, be purified by conventional means, for example vacuum distillation, optical resolution, thin layer or column or high-pressure liquid chromatography on silica gel, or may be used in a subsequent reaction without purification.

Compounds of general formula X, recovered from the reaction mixture, (in the case of the S- or R-isomer, without any noticeable loss of optical purity) can be used again as a starting material for the preparation of compounds of general formula IX thereby reducing the cost of using the reducing agents of the present invention.

Preferred compounds of the present invention are as follows:

lithium S-1,1'-binaphthyl-2,2'-dioxymethoxyaluminium hydride, lithium S-1,1'-binaphthyl-2,2'-dioxyethoxyaluminium hydride, lithium S-1,1'-binaphthyl-2,2'-dioxypropoxyaluminium hydride, lithium S-1,1'-binaphthyl-2,2'-dioxyisopropoxyaluminium hydride,
lithium S-1,1'-binaphthyl-2,2'-dioxy(tert-butoxy)aluminium hydride,
lithium S-1,1'-binaphthyl-2,2'-dioxy(2,2,2-trifluoroethoxy)aluminium hydride,
lithium S-1,1'-binaphthyl-2,2'-dioxy(2-hydroxyethoxy)aluminium hydride,
lithium S-1,1'-binaphthyl-2,2'-dioxy(2-methoxyethoxy)aluminium hydride,
lithium S-1,1'-binaphthyl-2,2'-dioxy(2,6-di-tert-butylphenoxy)aluminium hydride,
and their 3,3'-dimethyl or 3,3'-diethyl derivatives, and their R-isomers, and their racemates.

The following compounds are particularly preferred:
lithium R-1,1'-binaphthyl-2,2'-dioxymethoxyaluminium hydride,
lithium S-1,1'-binaphthyl-2,2'-dioxymethoxyaluminium hydride,
lithium R-1,1'-binaphthyl-2,2'-dioxyethoxyaluminium hydride,
lithium S-1,1'-binaphthyl-2,2'-dioxyethoxyaluminium hydride,
lithium R-1,1'-binaphthyl-2,2'-dioxypropoxyaluminium hydride,
lithium R-1,1'-binaphthyl-2,2'-dioxyisopropoxyaluminium hydride,
lithium R-1,1'-binaphthyl-2,2'-binaphthyl-2,2'-dioxy(tert-butoxy)aluminium hydride,
lithium S-1,1'-binaphthyl-2,2'-dioxy(2,2,2-trifluoroethoxy)aluminium hydride,
lithium R-1,1'-binaphthyl-2,2'-dioxy(2-hydroxyethoxy)aluminium hydride,
lithium R-1,1'-binaphthyl-2,2'-dioxy(2-methoxyethoxy)aluminium hydride,
lithium S-1,1'-binaphthyl-2,2'-dioxy(2-methoxyethoxy)aluminium hydride,
lithium R-1,1'-binaphthyl-2,2'-dioxy(2,6-di-tert-butylphenoxy)aluminium hydride,
lithium R-1,1'-binaphthyl-3,3'-dimethyl-2,2'-dioxymethoxyaluminium hydride and
lithium R-1,1'-binaphthyl-3,3'-dimethyl-2,2'-dioxypropoxyaluminium hydride.

The following Reference Examples and Examples illustrate the preparation of compounds of the present invention and their use. In the Reference Examples and Examples "TLC", "IR" and "NMR" represent respectively "Thin layer chromatography", "Infrared absorption spectrum" and "Nuclear magnetic resonance spectrum". Where solvent ratios are specified in chromatographic separations, the ratios are by volume; the solvents in parentheses show the developing solvent used. Except when specified otherwise, infrared spectra are recorded by the liquid film method, and nuclear magnetic resonance spectra are recorded in carbon tetrachloride ($CCl_4$) solution.

REFERENCE EXAMPLE 1

R-2,2'-Dimethoxy-1,1'-binaphthyl

A solution of 465 mg of R-2,2'-dihydroxy-1,1'-binaphthyl in 10 ml of tetrahydrofuran was added to a suspension of 1.35 g of potassium hydride in mineral oil (content 22.5% w/w) with cooling in an ice-bath and the mixture was stirred at room temperature for one hour. To the solution obtained was added a solution of 2.00 ml of methyl iodide in 4 ml of tetrahydrofuran, and the mixture was stirred at ambient temperature for 16 hours. The reaction mixture was poured into 100 ml of a mixture of benzene and water (1:1), and separated into an aqueous layer and an organic layer. The aqueous layer was extracted with benzene, and the extract was combined with the organic layer, washed with a saturated aqueous solution of sodium chloride, dried over sodium sulphate and concentrated under reduced pressure. The residue was purified by recrystallisation from a mixture of benzene and hexane to give 461 mg of the title compound as white crystals having the following physical characteristics: melting point: 225°–226° C.;
$[\alpha]_D^{21} = +72.0°$ (c=0.286, tetrahydrofuran).

REFERENCE EXAMPLE 2

R-2,2'-Dimethoxy-3,3'-dimethyl-1,1'-binaphthyl

To 3.1 ml of N,N,N',N'-tetramethylethylenediamine was added 13.6 ml of a 1.47 M solution of butyllithium in hexane with cooling in an ice-bath. The mixture was stirred at room temperature for one hour. To the solution obtained was added a solution of 800 mg of R-2,2'-dimethoxy-1,1'-binaphthyl (prepared as described in Reference Example 1) in 25 ml of tetrahydrofuran with cooling in an ice-bath, and the mixture stirred at 45° C. for 2 hours. 1.3 ml of methyl iodide was added to the mixture, with cooling in an ice-bath, and the reaction mixture was then stirred at laboratory temperature for 14 hours. The reaction mixture was poured into a mixture of 100 ml of 2 N hydrochloric acid and 50 ml of benzene, the organic layer was separated, washed with a saturated aqueous solution of sodium chloride, dried over sodium sulphate and concentrated under reduced pressure. The residue was purified by recrystallisation from a mixture of ethyl acetate and hexane (1:2) to give 540 mg of the title compound as yellow plate-like crystals having the following physical characteristics:
melting point: 176°–177° C.;
$[\alpha]_D^{24} = -104°$ (c=1.01, chloroform).

REFERENCE EXAMPLE 3

R-2,2'-Dihydroxy-3,3'-dimethyl-1,1'-binaphthyl

To a solution of 22.9 mg of R-2,2'-dimethoxy-3,3'-dimethyl-1,1'-binaphthyl (prepared as described in Reference Example 2) in 4 ml of methylene chloride was added 0.5 ml of a 1.0 M solution of boron tribromide in methylene chloride at −78° C., and the mixture was stirred at the same temperature for 20 minutes, then at room temperature for 30 minutes. The reaction mixture was poured into a mixture of 30 ml of water and 30 ml of methylene chloride, and separated into an organic layer and an aqueous layer. The organic layer was extracted with 3 N aqueous sodium hydroxide, and the extract combined with the previously obtained aqueous layer. The aqueous solution was acidified with 6 N hydrochloric acid, and then extracted with benzene. The benzene extract was concentrated under reduced pressure to give 15.8 mg of the title compound as white crystals having the following physical characteristics:
melting point: 196°–198° C.;
$[\alpha]_D^{22} = +37.2°$ (c=0.296, chloroform).

EXAMPLE 1

Lithium R-1,1'-binaphthyl-2,2'-dioxyethoxyaluminium hydride in tetrahydrofuran solution [Reagent (A)]

Under an atmosphere of nitrogen, a mixture of 2.75 ml of a 1.0 M solution of lithiumaluminium hydride in tetrahydrofuran, 2.80 ml of a 1.0 M solution of ethanol in tetrahydrofuran and a solution of 787 mg of R-2,2'- dihydroxy-1,1'-binaphthyl in 5.5 ml of tetrahydrofuran was stirred at 30° C. for 13.5 hours with the evolution of 184.8 ml of hydrogen to give the title solution (0.249 M). By proceeding in a similar manner, but replacing the ethanol by the appropriate alcohol R²OH, wherein R² is as hereinbefore described, the tetrahydrofuran solutions of the following compounds were prepared; the numbers in parentheses show the reaction time (hours).

reagent(B): lithium R-1,1'-binaphthyl-2,2'-dioxymethoxyaluminium hydride (5.5).

reagent(C): lithium R-1,1'-binaphthyl-2,2'-dioxypropoxyaluminium hydride (14).

reagent(D): lithium R-1,1'-binaphthyl-2,2'-dioxyisopropoxyaluminium hydride (13.5).

reagent(E): lithium R-1,1'-binaphthyl-2,2'-dioxy(2,6-ditert-butylphenoxy)aluminium hydride (12).

reagent(F): lithium R-1,1'-binaphthyl-3,3'-dimethyl-2,2'-dioxymethoxyaluminium hydride (18); (using as starting material R-2,2'-dihydroxy-3,3'-dimethyl-1,1'-binaphthyl, prepared as described in Reference Example 3).

reagent(G): lithium R-1,1'-binaphthyl-2,2'-dioxy(2-methoxyethoxy)aluminium hydride (12.5).

reagent(H): lithium R-1,1'-binaphthyl-2,2'-dioxy(tert-butoxy)aluminium hydride (12.5).

reagent(I): lithium R-1,1'-binaphthyl-2,2'-dioxy(2-hydroxyethoxy)aluminium hydride (22).

reagent(J): lithium R-1,1'-binaphthyl-3,3'-dimethyl-2,2'-dioxypropoxyaluminium hydride (20); (using as starting material R-2,2'-dihydroxy-3,3'-dimethyl-1,1'-binaphthyl, prepared as described in Reference Example 3).

EXAMPLE 2

Lithium S-1,1'-binaphthyl-2,2'-dioxyethoxyaluminium hydride in tetrahydrofuran solution [reagent (K)]

Under an atmosphere of nitrogen, a mixture of 0.50 ml of a 0.248 M solution of lithiumaluminium hydride in tetrahydrofuran, 0.50 ml of a 0.25 M solution of ethanol in tetrahydrofuran, and 1.00 ml of a 0.126 M solution of S-2,2'-dihydroxy-1,1'-binaphthyl in tetrahydrofuran was stirred at room temperature for one hour with the evolution of 8.3 ml of hydrogen gas to give the 0.062 M title solution. The title solution was concentrated under reduced pressure to give a white powder having the following physical characteristics:- m.p. >300° C.

IR (nujol): $\nu = 3045, 1610, 1592, 1060$ cm$^{-1}$.

By proceeding in a similar manner, but replacing the ethanol by the appropriate alcohol the tetrahydrofuran solutions of the following compounds were prepared; the numbers in parentheses show the reaction time (hours).

reagent(L): lithium S-1,1'-binaphthyl-2,2'-dioxy(2,2,2-trifluoroethoxy)aluminium hydride (1.0).

reagent(M): lithium S-1,1'-binaphthyl-2,2'-dioxymethoxyaluminium hydride (22).

reagent(N): lithium S-1,1'-binaphthyl-2,2'-dioxy(2-methoxyethoxy)aluminium hydride (8).

The reagent solutions A to J, L, M and N prepared in Examples 1 and 2 all yield, on concentration under reduce pressure, white powders having melting points above 300° C.

EXAMPLE 3

Reduction of acetophenone

Under an atmosphere of nitrogen, 1.80 ml of a 0.99 M solution of acetophenone in tetrahydrofuran was added to the solution of reagent (A), obtained in Example 1, and the mixture stirred at 30° C. for 24 hours. The reaction mixture was poured into a mixture of 15 ml of benzene and 10 ml of 2 M hydrochloric acid, extracted with benzene, and the extract was washed with water, dried over sodium sulphate and concentrated under reduced pressure. The residue was purified by distillation in vacuo (130°–135° C./25 mmHg) to give 185 mg of 1-phenylethanol, and an additional purification was carried out by a fractional gas chromatography to give 1-phenylethanol having the following optical rotation:

$[\alpha]_D^{25} = +47.2°$ (c=1.13, cyclopentane);

optical purity: 81% (R).

The optical purity values in this specification were calculated according to the following formula:

$$\text{Optical purity}(\%) = \frac{\text{optical rotation of a product}}{\text{optical rotation of the corresponding optically pure compound}} \times 100$$

Acetophenone was reduced with other reagents prepared as described in Examples 1 and 2, in the same manner as described above, to give the results shown in the following Table 1.

TABLE 1

| Reagent | Reduction Temperature (°C.) | Reduction Time (hours) | Chemical Yield (%) | Optical Purity (%) (R or S) |
|---|---|---|---|---|
| (B) | 30 | 15 | 64 | 76(R) |
| (C) | 30 | 2 | 88 | 70(R) |
| (D) | 30 | 2 | 100 | 41(R) |
| (E) | 30 | 3.5 | — | 41(S) |
| (F) | 70 | 18 | — | 70(R) |
| (K) | −100 | 3 | | |
| | −78 | 14 | 55 | 95(S) |
| (K)* | −100 | 2 | | |
| | −78 | 16 | 53 | 93(S) |
| (L) | −100 | 2 | | |
| | −78 | 16 | 70 | 46(R) |

*Reduced in the presence of one equivalent of N,N,N',N'-tetramethylethylenediamine.

Two equivalents of reagents B, C, D, E and F, and three equivalents of reagents K and L, were used.

EXAMPLE 4

Ketones of the formula

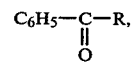

wherein R is as defined below in Table 2, were reduced with reagent (A) (prepared as described in Example 1) in the same manner as described in Example 3 to give the results shown in Table 2. Two equivalents of the reagent were used for each reduction.

TABLE 2

| Ketone R | Reduction Temperature (°C.) | Reduction Time (hours) | Optical Purity (%) (R or S) |
|---|---|---|---|
| —D | −100 | 3 | 87(R) |
| —C₂H₅ | 30 | 5 | 81(R) |
| —C₃H₇ | 30 | 1.2 | 87(R) |
| —C₄H₉ | 30 | 2 | 74(R) |

EXAMPLE 5

Ketones of the formula

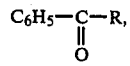

wherein R is as defined below in Table 3, were reduced with reagent (K) (prepared as described in Example 2) in the same manner as described in Example 3 to give the results shown in Table 3. Three equivalents of the reagent were used for each reduction.

TABLE 3

| Ketone R | Reduction Temperature (°C.) | Reduction Time (hours) | Chemical Yield (%) | Optical purity (%) (R or S) |
|---|---|---|---|---|
| —C$_2$H$_5$ | −100 | 3* | | |
| | −78 | 16 | 54 | 98(S) |
| —C$_3$H$_7$ | −100 | 3* | | |
| | −78 | 16 | 78 | 100(S) |
| -iso- C$_3$H$_7$ | −100 | 3* | | |
| | −78 | 16 | 52 | 71(S) |
| —C$_4$H$_9$ | −100 | 3* | | |
| | −78 | 16 | 46 | 100(S) |

*The reduction was allowed to proceed at −100° C. for 3 hours and then for 16 hours at −78° C.

EXAMPLE 6

Reduction of 4-tert-butylcyclohexanone 4-tert-Butylcyclohexanone was reduced with the reagents (prepared as described in Example 1) in the same manner as described in Example 3 to give the results shown in Table 4. The ratio of cis-form and trans-form was determined by gas chromatography.

TABLE 4

| Reagent | Reduction Temperature (°C.) | Reduction Time (hours) | cis:trans* |
|---|---|---|---|
| (B) | −90→ room temp. | overnight | 85:15 |
| (G) | 30 | 3 | 55:45 |
| (A) | 30 | 1 | 73:27 |
| (H) | 30 | 24 | 32:68 |
| (E) | 30 | 1.3 | 34:66 |
| (I) | 30 | 20 | 81:19 |

*cis-form: cis-4-tert-butylcyclohexanol trans-form: trans-4-tert-butylcyclohexanol When reagent (B) was used the temperature of the reaction mixture was allowed to rise from −90° C. to room temperature overnight. Two equivalents of each reagent were used.

EXAMPLE 7

The ketones of the prostaglandin intermediates specified below were reduced with reagent (K) (prepared as described in Example 2) in the same manner as described in Example 3 to give the results shown in Table 5. Purification was carried out by column chromatography on silica gel instead of distillation under vacuum, and the ratio of α-form and β-form was determined by high-pressure liquid chromatography using a JASCO's "TRIROTAR" instrument. Three equivalents of the reagent were used for each reduction.

TABLE 5

| Ketone | Reduction Temperature (°C.) | Reduction Time (hours) | Chemical Yield (%) | α-form:β-form |
|---|---|---|---|---|
| [1] | −78 | 2 | 44 | 96:4 |
| [2] | −78 | 2 | 39 | 100:0 |
| [3] | −78 | 2 | 26 | 100:0 |
| [4] | −78 to −40 | 3* | 92 | 88:12 |

*The temperature was allowed to rise from −78° C. to −40° C. during the course of the 3 hours.

[1]: (E)-2-oxa-6-syn-(3-oxo-oct-1-enyl)-7-anti-(tetrahydropyran-2-yloxy)-cis-bicyclo[3.3.0]octan-3-one
α-form: (E)-2-oxa-6-syn-(3α-hydroxy-1-enyl)-7-anti-(tetrahydropyran-2-yloxy)-cis-bicyclo[3.3.0]octan-3-one
β-form: (E)-2-oxa-6-syn-(3β-hydroxy-1-enyl)-7-anti-(tetrahydropyran-2-yloxy)-cis-bicyclo[3.3.0]octan-3-one
[2]: (5Z,13E)-(9α,11α)-9,11-bis(tetrahydropyran-2-yloxy)-15-oxoprosta-5,13-dienoic acid methyl ester
α-form: (5Z,13E)-(9α,11α,15α)-9,11-bis(tetrahydropyran-2-yloxy)-15-hydroxyprosta-5,13-dienoic acid methyl ester
β-form: (5Z,13E)-(9α,11α,15β)-9,11-bis(tetrahydropyran-2-yloxy)-15-hydroxyprosta-5,13-dienoic acid methyl ester
[3]: (E)-2-oxa-6-syn-(3-oxo-oct-1-enyl)-7-anti-hydroxy-cis-bicyclo[3.3.0]octan-3-one
α-form: (E)-2-oxa-6-syn-(3β-hydroxyoct-1-enyl)-7-anti-hydroxy-cis-bicyclo[3.3.0]octan-3-one
β-form: (E)-2-oxa-6-syn-(3β-hydroxyoct-1-enyl)-7-anti-hydroxy-cis-bicyclo[3.3.0]octan-3-one
[4]: (E)-2-oxa-6-syn-(3-oxo-oct-1-enyl)-7-anti-acetoxy-cis-bicyclo[3.3.0]octan-3-one
α-form: (E)-2-oxa-6-syn-(3α-hydroxyoct-1-enyl)-7-anti-acetoxy-cis-bicyclo[3.3.0]octan-3-one
β-form: (E)-2-oxa-6-syn-(3β-hydroxyoct-1-enyl)-7-anti-acetoxy-cis-bicyclo[3.3.0]octan-3-one

EXAMPLE 8

(+)-S-1-Iodo-oct-trans-1-en-3-ol

Under an atmosphere of nitrogen, a solution of 118 mg of 1-iodo-oct-trans-1-en-3-one in 2 ml of tetrahydrofuran was added dropwise over a period of 10 minutes to 7.6 ml of a 0.184 M solution of reagent (K) (prepared as described in Example 2) in tetrahydrofuran at −100° C., and stirred at the same temperature for 2 hours, and then at −78° C. for one hour. The reaction mixture was stirred with 40 ml of diethyl ether and 0.3 ml of water at room temperature for 30 minutes, dried over magnesium sulphate, filtered through a pad of infusorial earth, and the filtrate was concentrated under reduced pressure. The residue was dissolved in hexane, filtered, and the filtrate was concentrated under reduced pressure. The residue was purified by column chromatography on silica gel using a mixture of petroleum ether and diethyl ether (4:1) as eluent to give 113 mg of the title compound having the following physical characteristics:

boiling point: 135° C./2 mmHg;
$[\alpha]_D^{24} = +9.53°$ (c=1.53, methanol);
IR: $\nu$=3320, 3040, 2960, 2920, 2860, 1610, 948 cm$^{-1}$;
NMR: $\delta$=0.92 (3H,t,J=7 Hz), 1.38 (8H,m), 2.10 (1H, broad s), 4.04 (2H,m), 6.28 (1H,d,J=15 Hz), 6.54 (1H,dd,J=15 and 6 Hz);

| elemental analysis as C$_8$H$_{15}$IO: | | |
|---|---|---|
| | C(%) | H(%) |
| calculated: | 37.81 | 5.95 |
| found: | 37.52 | 5.69 |

(+)-S-1-Bromo-oct-trans-1-en-3-ol (980 mg), having the following physical characteristics, was prepared from 1-bromo-oct-trans-1-en-3-one (1.081 g) by the same procedure as described above:

boiling point: 105° C./1 mmHg;
$[\alpha]_D^{24} = +12.6°$ (c=1.40, methanol);
TLC (petroleum ether:diethyl ether=1:1): Rf=0.50;
IR: $\nu$=3320, 1620, 936 cm$^{-1}$;
NMR: $\delta$=0.92 (3H,t,J=7 Hz), 1.32 (8H,m), 1.80 (1H, broad s), 4.06 (1H,m), 6.26 (2H,m);

| elemental analysis as $C_8H_{15}BrO$: | | |
|---|---|---|
| | C(%) | H(%) |
| calculated | 46.39 | 7.30 |
| found: | 46.53 | 7.16 |

The optical purity of the (+)-S-1-iodo-oct-trans-1-en-3-ol obtained was 97%: the optical purity of the (+)-S-1-bromo-oct-trans-1-en-3-ol obtained was 96%.

I claim:

1. A lithium 1,1'-binaphthyl-2,2'-dioxyaluminium hydride compound of the general formula:

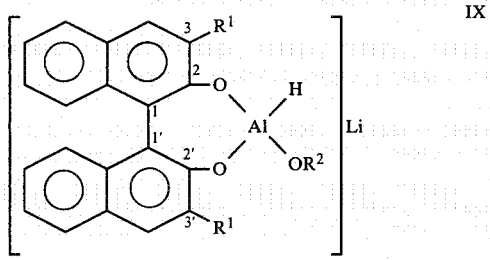

IX wherein $R^1$ represents a hydrogen atom, or a methyl or ethyl group, and $R^2$ represents a straight- or branched-chain alkyl group containing from 1 to 12 carbon atoms unsubstituted or substituted by at least one fluorine atom, hydroxy group, or straight- or branched-chain alkoxy group containing from 1 to 4 carbon atoms, or represents a phenyl group unsubstituted or substituted by at least one straight- or branched-chain alkyl group containing from 1 to 4 carbon atoms.

2. A compound according to claim 1 wherein $R^1$ represents a hydrogen atom or a methyl group.

3. A compound according to claim 1 wherein $R^2$ represents a straight- or branched-chain alkyl group containing from 1 to 12 carbon atoms or an alkyl group containing from 2 to 4 carbon atoms substituted by at least one fluorine atom or by a hydroxy or straight- or branched-chain alkoxy group containing from 1 to 4 carbon atoms, or represents a phenyl group substituted by two straight- or branched-chain alkyl groups each containing from 1 to 4 carbon atoms.

4. A compound according to claim 1 wherein $R^2$ represents a straight- or branched-chain alkyl group containing from 1 to 4 carbon atoms.

5. A compound according to claim 1 wherein $R^2$ represents a methyl or ethyl group.

6. A compound according to claim 1 which is lithium R-1,1'-binaphthyl-2,2'-dioxymethoxyaluminium hydride.

7. A compound according to claim 1 which is lithium-R-1,1'-binaphthyl-2,2'-dioxyethoxyaluminium hydride.

8. A compound according to claim 1 which is lithium R-1,1'-binaphthyl-2,2'-dioxypropoxyaluminium hydride.

9. A compound according to claim 1 which is lithium R-1,1'-binaphthyl-2,2'-dioxyisopropoxyaluminium hydride.

10. A compound according to claim 1 which is lithium R-1,1'-binaphthyl-2,2'-dioxy(tert-butoxy)aluminium hydride.

11. A compound according to claim 1 which is lithium R-1,1'-binaphthyl-2,2'-dioxy(2-hydroxyethoxy)aluminium hydride.

12. A compound according to claim 1 which is lithium R-1,1'-binaphthyl-2,2'-dioxy(2-methoxyethoxy)aluminium hydride.

13. A compound according to claim 1 which is lithium R-1,1'-binaphthyl-2,2'-dioxy(2,6-di-tert-butylphenoxy)aluminium hydride.

14. A compound according to claim 1 which is lithium R-1,1'-binaphthyl-3,3'-dimethyl-2,2'-dioxymethoxyaluminium hydride.

15. A compound according to claim 1 which is lithium R-1,1'-binaphthyl-3,3'-dimethyl-2,2'-dioxypropoxyaluminium hydride.

16. A compound according to claim 1 which is lithium S-1,1'-binaphthyl-2,2'-dioxymethoxyaluminium hydride.

17. A compound according to claim 1 which is lithium S-1,1'-binaphthyl-2,2'-dioxyethoxyaluminium hydride.

18. A compound according to claim 1 which is lithium S-1,1'-binaphthyl-2,2'-dioxy(2-methoxyethoxy)aluminium hydride.

19. A compound according to claim 1 which is lithium S-1,1'-binaphthyl-2,2'-dioxy(2,2,2-trifluoroethoxy)aluminium hydride.

20. The S isomers of the compound named in claims 8 to 11 and 13 to 15 and the R isomer of the compound named in claim 19.

21. A solution comprising a compound as claimed in claim 1 in an anhydrous inert organic solvent.

22. A solution according to claim 21 in which the solvent is an aprotic solvent.

23. A solution according to claim 21 in which the solvent is diethyl ether, tetrahydrofuran or diglyme.

24. A solution according to claim 21 comprising a compound as claimed in any one of claims 6 to 19 in anhydrous tetrahydrofuran.

* * * * *